(12) United States Patent
Chu et al.

(10) Patent No.: US 12,037,629 B2
(45) Date of Patent: Jul. 16, 2024

(54) ENGINEERED BIOCATALYSTS FOR NON-STERILE CULTIVATION AND SOLVENT-FREE BIOLIPID BIOEXTRACTION

(71) Applicant: The Texas A&M University System, College Station, TX (US)

(72) Inventors: Kung-Hui Chu, College Station, TX (US); Ry Young, College Station, TX (US); Jason Gill, College Station, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 17/407,939

(22) Filed: Aug. 20, 2021

(65) Prior Publication Data

US 2022/0056492 A1  Feb. 24, 2022

Related U.S. Application Data

(60) Provisional application No. 63/068,209, filed on Aug. 20, 2020.

(51) Int. Cl.
*C12P 7/6463* (2022.01)
*C12R 1/365* (2006.01)

(52) U.S. Cl.
CPC ...... *C12P 7/6463* (2013.01); *C12R 2001/365* (2021.05)

(58) Field of Classification Search
CPC .. C12P 7/6463; C12P 7/625; C12R 2001/365; C12N 1/06
See application file for complete search history.

(56) References Cited

PUBLICATIONS

Anthony et al., Development of Rhodococcus opacus as a chassis for lignin valorization and bioproduction of high-value compounds. Biotechnol Biofuels, 2019, vol. 12:192, pp. 1-14. (Year: 2019).*
Gill et al., Characterization of a Novel Tectivirus Phage Toil and Its Potential as an Agent for Biolipid Extraction. Nature, Scientific Reports, 2018, vol. 8:1062, pp. 1-11. (Year: 2018).*
Saier et al., Holins in Bacteria, Eukaryotes, and Archaea: Multifunctional Xenologues with Potential Biotechnological and Biomedical Applications. J. Bacteriol., 2015, vol. 197(1): 7-17 (Year: 2015).*
Wtodarczyk et al., Newly discovered *Synechococcus* sp. PCC 11901 is a robust cyanobacterial strain for high biomass production. Commun. Biol., 2020, vol. 3:215, pp. 1-14. (Year: 2020).*
Yang et al., Biodegradation of Di-(2-ethylhexyl) Phthalate by Rhodococcus ruber YC-YT1 in Contaminated Water and Soil. Int. J. Environ. Res. Public Health, 2018, vol. 15, 964, pp. 1-20. (Year: 2018).*
Hwangbo, M. et al. Application of Lysis Proteins from Mycobacteriophage D29 to lyse Rhodococcus opacus PD631 for Lipid Release. Texas Phage 2017 abstract and poster (presented at the Oct. 2017 Texas Phage 2017 Symposium hosted by the American Society for Microbiology).
Hwangbo, M. et al. Non-sterile triacylglycerols (TAGs) production by a salt-tolerant Rhododococcus opacus PD631. 2019 AEESP abstract and poster (presented at the May 2019 Association of Environmental Engineering and Science Professors conference).
Hwangbo, M. et al. Non-sterile triacylglycerol (TAG) production and extraction by a salt-tolerant Rhodococcus opacus PD631 containing a phage lytic cassette. 2019 C3E abstract and poster (presented at the Nov. 2019 U.S. Clean Energy Education & Empowerment Symposium).

* cited by examiner

*Primary Examiner* — Ganapathirama Raghu
(74) *Attorney, Agent, or Firm* — Winstead PC (57) ABSTRACT

In an embodiment, the present disclosure pertains to an oleaginous bacterium. In some embodiments, the oleaginous bacterium includes lipids and at least one exogenous and inducible gene. In some embodiments, the exogenous and inducible gene encodes at least one protein capable of inducing lysis in the oleaginous bacterium to release the lipids. In an addition embodiment, the present disclosure pertains to a method of releasing lipids into an environment. In general, the method includes one or more of the following steps of: (1) introducing at least one oleaginous bacterium of the present disclosure to the environment; and (2) inducing expression of at least one exogenous gene in the oleaginous bacterium to thereby induce the expression of at least one protein. In some embodiments, the protein facilitates the lysis of the oleaginous bacterium and release of the lipids into the environment.

22 Claims, 5 Drawing Sheets
Specification includes a Sequence Listing.

SEQUENCE LISTING

```
<160> NUMBER OF SEQ ID NOS: 2

<210> SEQ ID NO 1
<211> LENGTH: 33
<212> TYPE: DNA
<213> ORGANISM: Artificial Sequence
<220> FEATURE:
<223> OTHER INFORMATION: AHB_NdeIFW Primer

<400> SEQUENCE: 1
taagggcata tgatgacgct catagtcaca cgc                               33

<210> SEQ ID NO 2
<211> LENGTH: 30
<212> TYPE: DNA
<213> ORGANISM: Artificial Sequence
<220> FEATURE:
<223> OTHER INFORMATION: AHB_NcoIRV Primer

<400> SEQUENCE: 2
tgcttaccat ggtcagatct gtcgtaggaa                                   30
```

ENGINEERED BIOCATALYSTS FOR NON-STERILE CULTIVATION AND SOLVENT-FREE BIOLIPID BIOEXTRACTION

CROSS-REFERENCE TO RELATED APPLICATIONS

This application claims priority to U.S. Provisional Patent Application No. 63/068,209, filed on Aug. 20, 2020. The entirety of the aforementioned application is incorporated herein by reference.

STATEMENT REGARDING FEDERALLY SPONSORED RESEARCH

This invention was made with government support under 1134488 awarded by the National Science Foundation. The government has certain rights in the invention.

BACKGROUND

Production cost of lipid-based biofuels remains high, in part, due to high cost of cultivation under sterilized conditions to avoid microbial contamination and expensive downstream processes for extracting triacylglycerols from the triacylglycerol-filled microorganisms. Various embodiments of the present disclosure seek to address the aforementioned disadvantages.

SUMMARY

In an embodiment, the present disclosure pertains to oleaginous bacteria. In some embodiments, the oleaginous bacteria include lipids and at least one exogenous and inducible gene. In some embodiments, the exogenous and inducible gene encodes at least one protein capable of inducing lysis in the oleaginous bacteria to release the lipids.

In an addition embodiment, the present disclosure pertains to a method of releasing lipids into an environment. In general, the method includes one or more of the following steps of: (1) introducing oleaginous bacteria to the environment; and (2) inducing expression of at least one exogenous gene in the oleaginous bacteria to thereby express at least one protein. In some embodiments, the protein facilitates the lysis of the oleaginous bacteria and release of the lipids into the environment.

DESCRIPTION OF THE DRAWINGS

FIGS. 3A and 3B illustrate demonstration of inducible lysis of PD631pAHB.

DETAILED DESCRIPTION

It is to be understood that both the foregoing general description and the following detailed description are illustrative and explanatory, and are not restrictive of the subject matter, as claimed. In this application, the use of the singular includes the plural, the word "a" or "an" means "at least one", and the use of "or" means "and/or", unless specifically stated otherwise. Furthermore, the use of the term "including", as well as other forms, such as "includes" and "included", is not limiting. Also, terms such as "element" or "component" encompass both elements or components comprising one unit and elements or components that include more than one unit unless specifically stated otherwise.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

Triacylglycerols, one type of biolipids, are starting materials for producing biolipid-based biofuels such as biodiesel and biojet fuel. Triacylglycerols can be produced from various microorganisms including microalgae, yeast, and bacteria. Compared to microalgae or yeast, cultivation of triacylglycerol-accumulating bacteria is much easier and sustainable as higher triacylglycerol yields can be produced from various inexpensive and renewable organic wastes. However, production cost of lipid-based biofuels remains high, in part, due to two additional major obstacles: (1) high cost of cultivation under sterilized conditions to avoid microbial contamination; and (2) expensive downstream processes for extracting triacylglycerols from the triacylglycerol-filled microorganisms.

Accordingly, a need exists for more effective lipid-releasing bacteria and methods of cultivating lipids (e.g., triacylglycerols) from bacteria. Various embodiments of the present disclosure address the aforementioned needs.

In some embodiments, the present disclosure pertains to oleaginous bacteria. In some embodiments, the oleaginous bacteria include lipids and at least one exogenous and inducible gene. In some embodiments, the exogenous and inducible gene encodes at least one protein capable of inducing lysis in the oleaginous bacteria to release the lipids.

Figure 1:
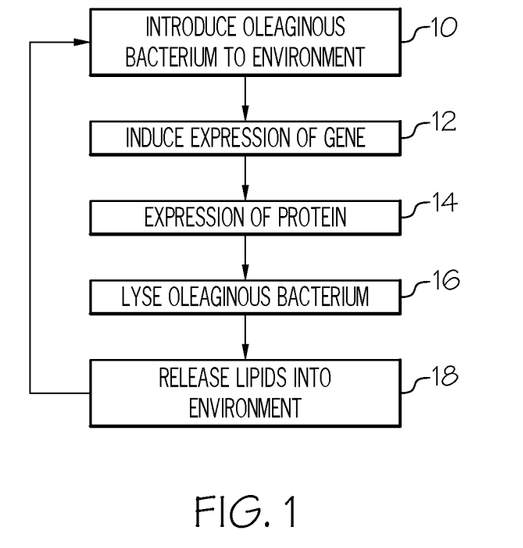
FIG. 1 illustrates a method of releasing lipids into an environment according to an aspect of the present disclosure.

Additional embodiments of the present disclosure pertain to methods of releasing lipids into an environment. In some embodiments illustrated in FIG. 1, the methods of the present disclosure include one or more of the following steps of: introducing oleaginous bacteria to the environment (step 10), inducing expression of at least one gene in the oleaginous bacteria (step 12) to result in the expression of at least one protein (step 14), lysing the oleaginous bacteria facilitated by the protein (step 16), and releasing of the lipids into the environment (step 18). In some embodiments, the methods of the present disclosure can be repeated until the desired number of lipids are released into the environment.

As set forth in more detail herein, the oleaginous bacteria and methods of the present disclosure can have numerous embodiments. For instance, the oleaginous bacteria of the present disclosure can include various lipids. In addition, the oleaginous bacteria of the present disclosure can include various exogenous and inducible genes that can encode various proteins capable of inducing lysis in the oleaginous bacteria to release the lipids. Furthermore, various methods may be utilized for releasing lipids into an environment.

Oleaginous Bacteria

As set forth in further detail herein, the oleaginous bacteria of the present disclosure include lipids and at least one exogenous and inducible gene. In some embodiments, the exogenous and inducible gene encodes at least one protein capable of inducing lysis in the oleaginous bacteria to release the lipids. As detailed herein, the oleaginous bacteria can include various lipids. Furthermore, numerous exogenous and inducible genes can be utilized to expresses various proteins capable of inducing lysis in the oleaginous bacteria to release the lipids. Moreover, various methods can utilize the oleaginous bacteria to release the lipids into the environment. In addition, the oleaginous bacteria of the present disclosure may have various advantageous properties.

Oleaginous Bacteria

Oleaginous bacteria generally refer to bacteria that accumulate at least 20 wt % of lipids on a cell dry weight basis. In some embodiments, the oleaginous bacteria of the present disclosure accumulate at least 25 wt % of lipids on a cell dry weight basis. In some embodiments, the oleaginous bacteria of the present disclosure accumulate at least 35 wt % of lipids on a cell dry weight basis. In some embodiments, the oleaginous bacteria of the present disclosure accumulate at least 50 wt % of lipids on a cell dry weight basis. In some embodiments, the oleaginous bacteria of the present disclosure accumulate more than 85 wt % of lipids on a cell dry weight basis. In some embodiments, the oleaginous bacteria of the present disclosure exhibit tolerance to salt. In some embodiments, the salt is NaCl. In some embodiments, the tolerance to salt is represented by a growth rate that is at least 10% similar when the oleaginous bacteria is grown at 30° C. in the presence or absence of at least 3% (w/v) salt. In some embodiments, the tolerance to salt is represented by a growth rate that is at least 5% similar when the oleaginous bacteria is grown at 30° C. in the presence or absence of at least 3% (w/v) salt. In some embodiments, the tolerance to salt is represented by a growth rate that is at least 1% similar when the oleaginous bacteria is grown at 30° C. in the presence or absence of at least 3% (w/v) salt. In some embodiments, the growth rate is represented by the doubling time of the oleaginous bacteria.

The oleaginous bacteria of the present disclosure can include various strains and species of bacteria. For example, in some embodiments, the oleaginous bacteria can include, without limitation, bacteria from *Rhodococcus* species, bacteria from *Nocardia* species, derivatives of *R. opacus*, high-salt tolerant strains of *R. opacus*, *R. opacus* strain PD631SpAHB, *R. opacus* strain PD631S, derivatives of *Nocardia* species, high-salt tolerant strains of *Nocardia* species, and combinations thereof.

In some embodiments, the oleaginous bacteria include *R. opacus*. In some embodiments, the oleaginous bacteria include a salt-tolerant strain of an oleaginous bacterium. In some embodiments, the salt-tolerant strain is *R. opacus* strain PD631SpAHB. In some embodiments, the salt-tolerant strain is *R. opacus* strain PD631S.

Lipids

As detailed herein, the oleaginous bacteria of the present disclosure can include various types of lipids in oleaginous bacteria. For example, in some embodiments, the lipids can include, without limitation, triacylglycerols, biolipids, polyhydroxyburyrate, and combinations thereof. In some embodiments, the lipids are triacylglycerols.

In some embodiments, the lipids are capable of being released from the oleaginous bacteria into an environment upon expression of a protein by an exogenous and inducible gene in the oleaginous bacteria. In some embodiments, the environment can include, without limitation, a supernatant, a high-salt environment, a non-sterile environment, and combinations thereof.

Exogenous and Inducible Gene and Expressed Protein

As set forth in further detail herein, the oleaginous bacteria of the present disclosure can include at least one exogenous and inducible gene that can encode at least one protein capable of inducing lysis in the oleaginous bacteria. For instance, in some embodiments, the exogenous and inducible gene encodes a protein that can include, without limitation, endolysin, holin, mycoesterase, lytic proteins, and combinations thereof. In some embodiments, the exogenous and inducible gene includes multiple genes. In some embodiments, the multiple genes are within a gene cassette.

In some embodiments, the exogenous and inducible gene encodes a lytic protein. In some embodiments, the lytic protein degrades a cell envelope of the oleaginous bacteria.

The exogenous and inducible genes in the oleaginous bacteria of the present disclosure can be derived from various sources. For instance, in some embodiments, the exogenous and inducible gene include at least one phage gene.

The exogenous and inducible genes in the oleaginous bacteria of the present disclosure can be located in various regions of the oleaginous bacteria. For instance, in some embodiments, the exogenous and inducible genes are on a plasmid. In some embodiments, the plasmid is an inducible plasmid. In some embodiments, the exogenous and inducible gene is integrated into a chromosome of the oleaginous bacteria. In some embodiments, the exogenous and inducible gene is located on an inducible prophage.

Method of Releasing Lipids into an Environment

The oleaginous bacteria of present disclosure can be utilized for various purposes. For instance, in some embodiments, the oleaginous bacteria of the present disclosure can be used for releasing lipids into an environment. In general, the method for releasing lipids into the environment can include one or more of the following steps of: (1) introducing at least one oleaginous bacteria to the environment; and (2) inducing expression of at least one exogenous gene in the oleaginous bacteria to thereby express at least one protein.

In some embodiments, the protein facilitates the lysis of the oleaginous bacteria and release of the lipids into the environment.

Introducing

As set forth in further detail herein, the methods of the present disclosure can utilize various methods to introduce oleaginous bacteria to an environment. For example, in some embodiments, the introducing includes inoculating the environment with the oleaginous bacteria. In some embodiments, the introducing includes pouring a pregrown batch of the oleaginous bacteria into the environment.

Environment

As detailed herein, the methods of the present disclosure can use the oleaginous bacteria of the present disclosure to release lipids into various environments. For example, in some embodiments, the environment can include, without limitation, a supernatant, a high-salt environment, a non-sterile environment, and combinations thereof. In some embodiments, the environment can include a natural environment, such as a field or habitat. In some embodiments, the environment can include a non-natural environment, such as a container.

In some embodiments, the environment is a non-sterile environment. In some embodiments, the non-sterile environment includes a salt concentration of at least 3% (w/v). In some embodiments, the non-sterile environment lacks antibiotics.

Oleaginous Bacteria

As set forth in further detail herein, the methods of the present disclosure can utilize various oleaginous bacteria. For instance, in some embodiments, the oleaginous bacteria can include, without limitation, *Rhodococcus* species, *Nocardia* species, derivatives of *R. opacus*, high-salt tolerant strains of *R. opacus*, *R. opacus* strain PD631SpAHB, *R. opacus* strain PD631S, derivatives of *Nocardia* species, high-salt tolerant strains of *Nocardia* species, and combinations thereof.

In some embodiments, the oleaginous bacteria include *R. opacus*. In some embodiments, the oleaginous bacteria include a salt-tolerant strain of the oleaginous bacteria. In some embodiments, the salt-tolerant strain is *R. opacus* strain PD631SpAHB. In some embodiments, the salt-tolerant strain is *R. opacus* strain PD631S.

Lipids

As detailed herein, the methods of the present disclosure can release various lipids into the environment. Suitable lipids were described previously in this application. For instance, in some embodiments, the lipids can include, without limitation, triacylglycerols, biolipids, polyhydroxyburyrate, and combinations thereof. In some embodiments, the lipids are triacylglycerols.

Gene and Protein

As set forth in further detail herein, the methods of the present disclosure can induce expression of various exogenous genes in oleaginous bacteria to express various proteins. Suitable genes and proteins were described previously in this application. For instance, in some embodiments, the gene expresses a protein that can include, without limitation, endolysin, holin, mycoesterase, lytic proteins, and combinations thereof. In some embodiments, the gene includes at least one phage gene.

In some embodiments, the gene is on a plasmid. In some embodiments, the plasmid is an inducible plasmid. In some embodiments, the gene is integrated into a chromosome of the oleaginous bacteria. In some embodiments, the gene is located in an inducible prophage.

Inducing

As outlined herein, the methods of the present disclosure can utilize various methods to induce the expression of exogenous genes in the oleaginous bacteria of the present disclosure. For example, in some embodiments, the inducing occurs by introducing an inducing agent into an environment. In some embodiments, the inducing agent includes isopropyl β-D-1-thiogalactopyranoside (IPTG).

In some embodiments, the inducing occurs by introducing an inducing condition into an environment. In some embodiments, the inducing condition includes a change in temperature of the environment. In some embodiments, the inducing condition includes a change in pressure of the environment.

Lysis and Release

As detailed herein, various methods can be utilized to promote lysis of the oleaginous bacteria in order to release the lipids from the oleaginous bacteria. For example, in some embodiments, the protein expressed from the exogenous genes of the oleaginous bacteria promote a lytic cycle to thereby degrade a cell envelope of the oleaginous bacteria and lyse the cells. In some embodiments, the release of the lipids into the environment occurs without use of a solvent.

Applications and Advantages

The present disclosure can have various advantages. For instance, in some embodiments, the oleaginous bacteria and methods of the present disclosure have at least the following valuable features: (1) the oleaginous bacteria of the present disclosure can release lipids (e.g., triacylglycerols) without using solvents; (2) the lipids of the present disclosure can be released in a non-sterile environment; (3) the lipids of the present disclosure can be released in a high-salt environment; and (4) the oleaginous bacteria and methods of the present disclosure can reduce the overall biolipid-based biofuel production costs.

Additionally, in some embodiments, the oleaginous bacteria of the present disclosure can include inducible lytic genes to enable cell lysis and lipid release on demand. In some embodiments, the oleaginous bacteria can accumulate lipids (e.g., triacylglycerols) in non-sterilized saline growth media.

As such, the oleaginous bacteria of the present disclosure can be utilized in various manners and for various purposes. For instance, in some embodiments, the oleaginous bacteria can be utilized for releasing lipids that can include, without limitation, triacylglycerols, biolipids, polyhydroxyburyrate, and combinations thereof.

In some embodiments, the methods of releasing lipids of the present disclosure can be optimized for biofuel production. In some embodiments, the methods of lipid release of the present disclosure offers new methods for biolipid extraction, leading to a reduction of overall extraction costs of biolipid for biofuel production. The oleaginous bacteria and methods for releasing lipids provide for eliminating high costs associated with sterilization cultivation and triacylglycerol extraction associated with current biolipid-based biofuel production.

Additional Embodiments

Reference will now be made to more specific embodiments of the present disclosure and experimental results that provide support for such embodiments. However, Applicants note that the disclosure below is for illustrative purposes only and is not intended to limit the scope of the claimed subject matter in any way.

Example 1. Dual-Function Oleaginous Biocatalysts for Non-Sterile Cultivation and Solvent-Free Biolipid Bioextraction to Reduce Biolipid-Based Biofuel Production Costs This Example describes dual-function oleaginous biocatalysts for non-sterile cultivation and solvent-free biolipid bioextraction to reduce biolipid-based biofuel production costs according to various aspects of the present disclosure.

Triacylglycerols (TAGs) are starting materials for the production of biolipid-based fuels such as biodiesel and biojet fuel. While various microorganisms can produce TAGs from renewable resources, the cultivation of TAG-producing microorganisms under sterilization conditions to avoid microbial contamination and application of solvent to extract TAGs from the TAG-filled microorganisms are costly. To overcome these challenges, this Example illustrates the feasibility of a non-sterile cultivation of an oleaginous bacterium *Rhodococcus opacus* PD631SpAHB under saline conditions, followed by the use of a solvent-free, phage-lysis-protein-based bioextraction approach for TAGs release. The engineered strain PD631SpAHB was developed by introducing a recombinant plasmid carrying a phage lytic gene cassette (pAHB) into *Rhodococcus opacus* PD631 via transformation, followed by adaptive evolution under saline conditions. This newly developed strain is a salt-tolerant strain with the inducible plasmid pAHB to enable TAGs release into the supernatant upon induction. Cell lysis of PD631SpAHB was confirmed by the decrease of the optical density of cell suspension, by the loss of cell membrane integrity, and by the detection of TAGs in the culture medium. Up to 38% of the total TAGs accumulated in PD631SpAHB was released into supernatant after the expression of the lytic genes. PD631SpAHB strain is a promising candidate to produce TAGs from non-sterile growth medium and release of its TAGs without solvent extraction—a new approach to reduce the overall cost of biolipid-based biofuel production.

Example 1.1. Introduction

Triacylglycerols (TAGs), one type of biolipids, are starting materials for producing biolipid-based biofuels such as biodiesel and biojet fuel. TAGs can be produced from various microorganisms including microalgae, yeast, and bacteria. Mostly, the production of bacterial TAGs is easy and sustainable, since high TAG yields from various inexpensive and renewable organic wastes are feasible. For example, *Rhodococcus opacus* PD630 (designated PD630 hereafter), a model strain capable of accumulating TAGs up to 76% of the cell dry weight, has been shown to produce TAGs from hydrolysates of renewable lignocellulosic biomass. However, the production cost of lipid-based biofuels remains high, in part, due to the two additional obstacles: the high cost of cultivation under sterilized conditions to avoid microbial contamination and the expensive downstream process for extracting TAGs from the TAG-filled microorganisms.

Sterilization of growth medium accounts for 16.4% of the total energy consumption of biolipid-based biofuel production. Accordingly, the non-sterile cultivation of biolipid-producing microorganisms is attractive and has been received considerable attention. One promising strategy to implement non-sterile cultivation is to leverage or create growth advantages for the desired strains to outgrow non-desired ones during the cultivation. For example, cultivation of salt-tolerant polyhydroxyburyrate (PHB)-accumulating strains in non-sterilized salt media for production of PHB, a type of biolipids, has been successfully demonstrated. The success of these studies relied on the fact that these salt-tolerant PHB-accumulating microbial strains can accumulate osmolytes such as glutamate, ectoine, or trehalose to survive under high saline conditions and outgrow those non-salt tolerant and non-PHB-accumulating strains. Accordingly, a similar strategy will be applicable to oleaginous strains for non-sterile cultivation in the saline growth medium, if the oleaginous strains become salt-tolerant. However, no study has explored this aspect—non-sterile saline cultivation of oleaginous bacterial strains for TAG production.

The high cost of extraction of biolipids from oleaginous microbes is another major obstacle, making the price of biolipid-based biofuels less competitive to those of petroleum-based fuels. While solvent extraction is a common method for biolipid extraction, this extraction method is considered as a bottleneck for commercial production of biolipid-based biofuels due to the toxicity of chlorinated solvent used in extraction, the requirement of additional energy input to separate biolipids from the solvent mixture, and the treatment cost for the spent solvent.

A novel bioextraction method using bacteriophage (phage) to lyse cells to release biolipids like PHB and TAGs has been recently reported. Bacteriophage, also called phage, is a host-specific bacterial virus. Once its DNA has invaded the bacterial host cell, the phage can enter a lytic cycle to degrade the cell envelope using phage-encoded lytic proteins, leading to release of the intracellular components upon cell lysis. However, achieving synchronous infection of the culture under the conditions of biomass growth is problematic.

Figure 2:
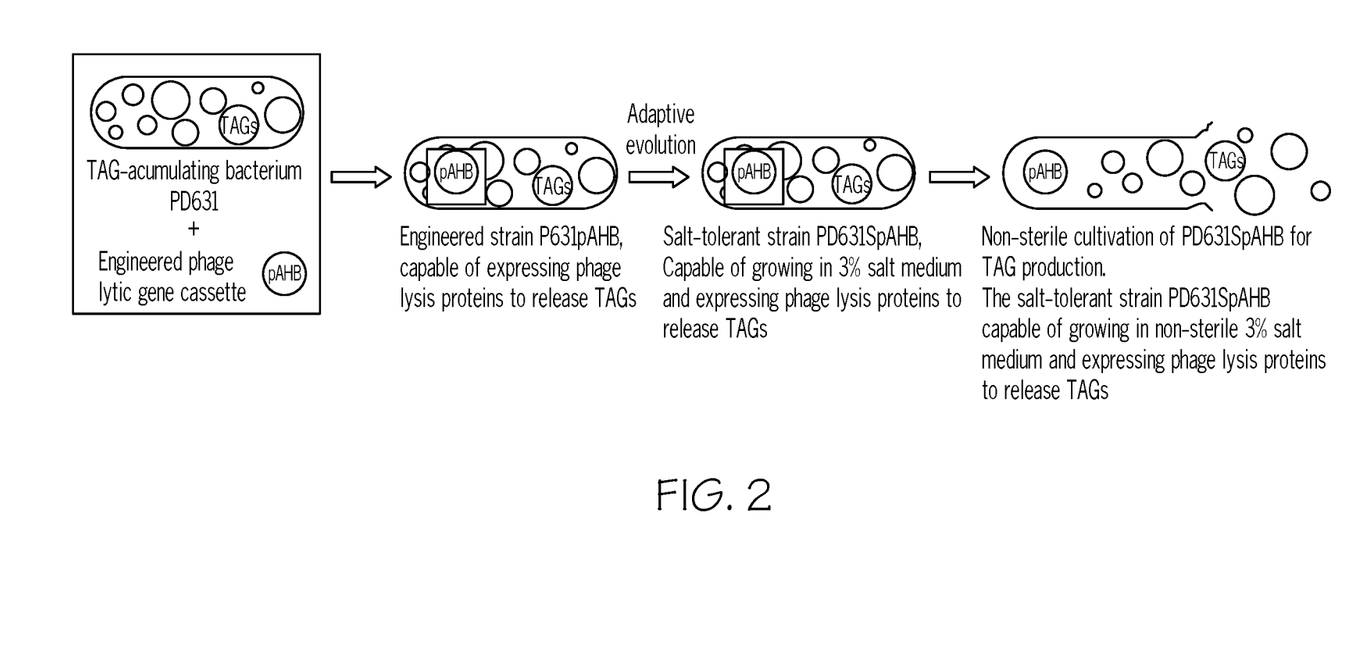
FIG. 2 illustrates a proposed experimental approach according to an aspect of the present disclosure.

In this Example, Applicant explored the development of a salt-tolerant TAG-accumulating bacterium with an ability to express phage lysis proteins by induction to achieve non-sterile cell cultivation and solvent-free bioextraction of TAGs from the TAG-filled bacterium (as shown in FIG. 2). First, an engineered TAG-producing bacterium with an ability to lyse cell by induction was developed by introducing an inducible phage lytic gene cassette into a known TAG-producing *R. opacus* PD631. Then, the engineered strain (designated PD631pAHB hereafter) was further developed via an adaptive evolution strategy to become a high-salt tolerant strain, PD631SpAHB. This PD631SpAHB strain was characterized for its ability to outgrow non-TAG-producing microorganisms in non-sterile saline growth media and to release of its TAGs into the supernatant upon induction.

Example 1.2. Bacterial Strain, Culture Conditions, and Chemicals

The strain PD631, a domesticated derivative of PD630, was used in this Example. PD631 was developed by subculturing on Reasoner's 2A (R2A) agar plates for six months and showed a similar TAG-accumulating ability to PD630. The strain PD631 was maintained aerobically in R2A or Luria-Bertani (LB) broth medium at 200 rpm at 30° C. Amido black, hexane, methanol, and Imperial™ protein stain were purchased from Fisher Scientific (Hampton, NH, USA). R2A broth was purchased from Teknova (Hollister, CA, USA). Difco LB broth, Difco LB agar, Difco R2A agar, Difco Nutrient Agar, polypepton, and beef extract powder were purchased from VWR (Radnor, PA, USA). Diethyl ether, glyceryl trioleate (TL), chloroform, thiostrepton, chloramphenicol (CAM), and all other chemicals used in this study were purchased from Millipore Sigma (Burlington, MA, USA).

Example 1.3. Construction of a Plasmid with a Phage Lytic Gene Cassette Under Inducible Control To express phage lysis proteins in TAG-accumulating *Rhodococcus* strains, the lytic genes of *mycobacterium* phage D29 were selected because *Mycobacterium* and *Rhodococcus* have similar cell envelope structure. The phage D29 lytic gene cassette contains the genes lysA-holin-lysB (Table 1A). Phage D29 was provided from Center for Phage Technology at Texas A&M University (College Station, TX). The genomic DNA of phage D29 was prepared, purified by Promega Wizard DNA cleanup kit (Promega, Madison, WI), and then used for PCR amplification. The lytic gene cassette was amplified using 2 primers as listed in Table 1B. The PCR product was cloned into a pTipQC2 plasmid (AIST Japan, Tokyo, Japan) using the NdeI-NcoI cloning site.

Table 1A, shown below, illustrates names and sizes of phage lysis enzymes and associated phage lytic genes of *mycobacterium* phage D29. Table 1B, shown below, illustrates primer sets used for traditional cloning of the phage lytic gene cassette (lysA-holin-lysB) into the plasmid pTipQC2 as plasmid pAHB.

TABLE 1A

| Target gene | Enzyme | Size (kb) | # of Amino acids | MW (kDa) |
|---|---|---|---|---|
| lysA | Endolysin A | 1.5 | 493 | 55 |
| holin | Holin | 0.5 | 141 | 15 |
| lysB | Mycolate esterase (Endolysin B) | 0.8 | 254 | 29 |

TABLE 1B

| Primers | Sequence | Primer Length (bp) | Tm (° C.) |
|---|---|---|---|
| AHB_NdeIFW | 5'-TAAGGGCATATGATGACGCTC ATAGTCACACGC-3' (SEQ ID NO: 1) | 33 | 64 |
| AHB_NcoIRV | 5'-TGCTTACCATGGTCAGATCTG TCGTAGGAA-3' (SEQ ID NO: 2) | 30 | 62 |

Example 1.4. Development of PD631pAHB by Transformation of Recombinant Plasmid The verified recombinant plasmid (pAHB) was transformed into PD631 via electroporation to obtain a new engineered strain, PD631pAHB. Transformation was done as described previously. Briefly, the recombinant plasmid (about 300 ng) was mixed with electrocompetent cells of PD631 and preincubated at 40° C. for 5 min. The electroporation was performed in electrocuvettes (gaps of 2 mm) by micropulser (Bio-Rad, Hercules, CA, USA) with the following settings: ec2: 2.5 kV, 600 ohm, and 25 µF. The electroporated cells were recovered outgrown in Nutrient Broth (NB) medium at 30° C. for 4 h, and then plated on an NB agar plate with 35 mg/L of CAM as a selective marker. The transformant colonies were visible after 3 to 5 days incubation at 30° C. About 45 colonies were screened and transformation efficiency was $3.8 \times 10^2$ cfu/µg.

Example 1.5. Development of a Salt-Tolerant Engineered Strain (PD631SpAHB) Via Adaptive Evolution Ectoine and glutamate are the two most common osmolytes in salt-tolerant bacteria. An ectoine synthesis gene cluster (ectA, ectB, and ectC) encoding ectoine synthesis proteins were found in PD630 genome based on Blast-P results against to the genome of a known salt-tolerant strain *Zobellella denitrificans* ZD1. Additionally, six possible glutamate synthases genes encoding glutamate synthesis proteins were directly identified in the genome of PD630 (CP003949.1 as an accession number of GenBank databases). Since these osmolyte-producing genes are present in strain PD630, Applicant hypothesized that both the domesticated strain PD631 and the engineered strain PD631pAHB also contain these genes.

Accordingly, an adaptive evolution approach was used to develop PD631SpAHB, a salt-tolerant version of PD631pAHB. Briefly, PD631pAHB was successively subcultured on LB medium agar containing 35 mg/L of CAM and 3% (w/v) NaCl and incubated at 30° C. After 3 days of incubation, colonies were observed and re-streaked on a new plate containing LB agar medium with 35 mg/L of CAM and 3% NaCl. This process was repeated ten times over a month. Similarly, PD631S, a salt-tolerant version of PD631, was developed by ten times of successive subculturing of PD631 on LB medium agar containing 3% NaCl. These newly developed salt-tolerant strains PD631S and PD631SpAHB were allowed to adjust to the high saline liquid medium.

Example 1.6. Assessment of Cell Lysis after Induction of pAHB in the Engineered Strains The success of cell lysis after induction of pAHB in the engineered strains (i.e., PD631pAHB and PD631SpAHB) was determined by observation of decrease of optical density and detection of lactate dehydrogenase (LDH) in the supernatant. LDH is a cytosolic enzyme in cells. When cell membranes are damaged and/or cells are lysed, LDH will be released into growth medium. As LDH remains stable extracellularly in solution, presence of LDH in the supernatant can be used as an indication of cell lysis. Also, produced phage lysis proteins were analyzed by sodium dodecyl sulfate polyacrylamide gel electrophoresis (SDS-PAGE).

Example 1.7. Expression Levels of Genes Encoding Enzymes Responsible for Producing Known Osmolytes Experiments were designed to quantify the expression of genes encoding osmolytes-producing enzymes in PD631S grown in medium with or without salts. Briefly, the strain was grown on 10 g/L of glucose in the presence or absence of 3% NaCl aerobically in 50 mL of ammonium mineral salts (AMS) medium with a minor modification (i.e., replacing ammonium chloride with ammonium sulfate at the same molarity) at 200 rpm at 30° C. When the cell density reached an OD600 of 2.0, cells were harvested for total RNA extraction, followed by cDNA synthesis using the extracted RNA and quantification of targeted genes using the synthesized cDNA.

Example 1.8. Non-Sterile Cultivation of PD631S for TAG Production

Experiments for this Example were conducted to examine whether TAGs can be produced from non-sterile cultivation of PD631 and PD631S. Non-sterile cultivation of both strains for TAG production were conducted via two-stage cultivation process as described previously, except that non-sterile saline (3% NaCl) growth medium was used. Strains (PD631 and PD631S) were cultured with 10 g/L of glucose in AMS medium at 200 rpm at 30° C. until stationary growth phase (above $OD_{600}$ of 2.0). These saturated cultures were used as inocula for non-sterile cultivation experiments. An aliquot of the saturated culture was added to 50 mL of sterile or non-sterile AMS medium containing 10 g/L of glucose with or without 3% NaCl, resulting an initial OD600 ~0.02. After the inoculated cultures were grown at 200 rpm at 30° C. until early stationary phase, the cell suspension was pelleted, resuspended in sterile or non-sterile nitrogen-free mineral salts medium (MS) containing 10 g/L of glucose, and then incubated at 30° C. without shaking for 24 h. This process was to allow TAG accumulation while minimize TAG utilization. After 24 h of incubation, 50 mL of cell culture was pelleted by centrifugation at 10,000 g for 10 min and the cell pellet was used for TAG measurement using thin layer chromatography (TLC) analysis as described previously.

Example 1.9. Non-Sterile Cultivation of PD631SpAHB for TAG Production and Release TAG production under non-sterile conditions and TAGs release were investigated using PD631SpAHB along with PD631pTipQC2 used as a positive control. The experiments for this Example were conducted similarly as described in the above section with some modification. Most protein expression from cloning vector are generally induced by adding an inducer at $OD_{600}$ of 0.6-1.0. However, PD631 can maximize TAGs accumulation ability during stationary phase under nitrogen limited conditions. Due to this limitation, previous studies cultivated TAG-filled PD631 under nitrogen-limit conditions first, followed by promoting cell growth through nitrogen source addition before infecting with Toil phages because most phages propagate on the growing cells. The infected cells were then able to produce lysis enzymes that resulted in cell lysis to release of TAGs to supernatant. Similarly, in this Example, after accumulation of TAGs from the strain under nitrogen limited conditions, the cell cultures returned to the active growth by adding additional nitrogen content (0.78 g/L of $(NH_4)_2SO_4$) and 1 µg/mL of thiostrepton to induce phage lytic genes in PD631SpAHB. Following overnight induction, the cell pellet and suspension were collected respectively by centrifugation at 10,000 g for 10 min and used for TAG measurement using TLC analysis.

Figure 3A:
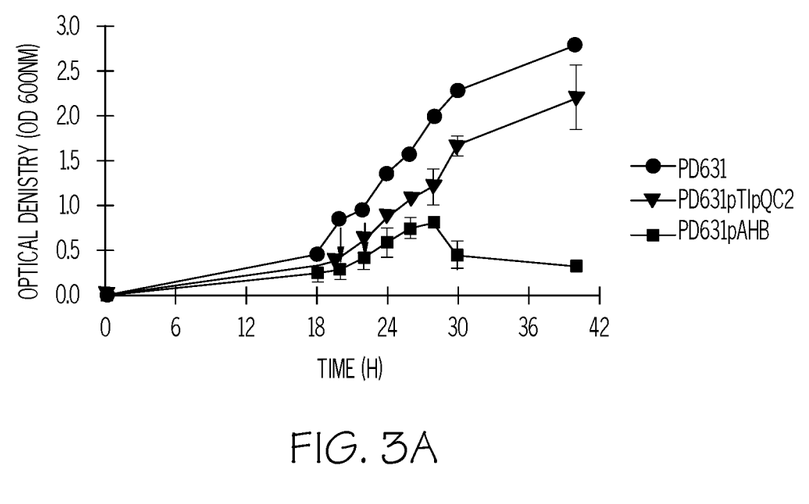
FIG. 3A shows a profile of the optical density before and after induction. Arrows indicate the time points (around OD600=0.5-0.7) where 1 µg/mL of thiostrepton was added as an inducer.

Example 1.10. Demonstration of Cell Lysis of PD631pAHB Via Induction of its Phage Lytic Gene Cassette An inducible plasmid pAHB for expressing phage lysis proteins was constructed by cloning the phage D29 lytic gene cassette (having genes lysA-holin-lysB) into the thiostrepton-inducible expression plasmid pTipQC2. The pAHB was then used to construct strain PD631pTipQC2 for cell lysis by induction. Cell lysis of PD631pAHB was confirmed by monitoring changes of cell density after inducing the expression of the phage lytic genes. As shown in FIG. 3A, PD631pTipQC2 and PD631pAHB both grew more slowly than R. opacus PD631 (designated PD631 hereafter). This might be due to CAM in the growth medium as a selective marker for both plasmids. However, PD631pAHB grew even more slowly than cells carrying an empty vector pTipQC2 (PD631pTipQC2), presumably due to leaky gene expression from the inducible promoter. After thiostrepton induction (1 µg/mL), cells carrying the empty vector continued to grow. However, the induced PD631pAHB culture showed decreased optical density after 6 h. The final optical density of PD631pAHB was ~0.3 after overnight induction.

Figure 3B:
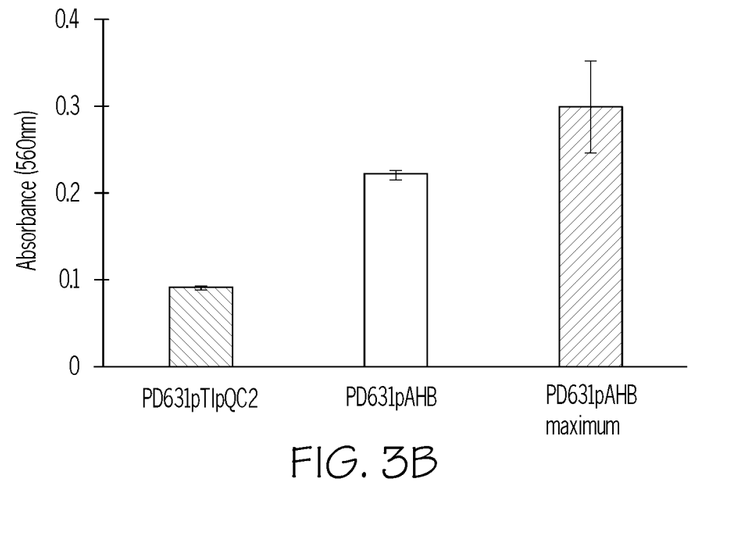
FIG. 3B shows lactate dehydrogenase (LDH) activity detected in the culture medium of PD631pTipQC2, PD631pAHB after induction, and PD631pAHB maximum. PD631pAHB maximum: designated PD631pAHB lysed by sonication artificially.

Additional experiments were conducted for this Example to characterize the lysis of the PD631pAHB cells using the release of a cytosolic enzyme, LDH into the growth medium. After pelleting cell debris and unlysed cells, the supernatant of the induced PD631pAHB cells had about 74% of the total LDH activity (FIG. 3B). Moreover, the expression of phage lytic genes in PD631pAHB was confirmed by visualizing the production of these lysis proteins on the SDS-PAGE gel. The protein profiles obtained from the concentrated whole-cell cultures and supernatant of PD631, PD631pTipQC2, and PD631pAHB were compared on the SDS-PAGE gel. Based on the predicted molecular masses of LysA, Holin, and LysB listed in Table 1A, three bands of the appropriate sizes were present in the sample from the induced cells carrying pAHB (lane 3) that were not present in the sample from the control: a thicker band for LysA (55 kDa) and two fainter bands for Holin (15 kDa) and LysB (29 kDa). Also, the sample of PD631pAHB after induction did not need additional cell lysis step (i.e., sonication), suggesting successful expression of the lytic gene cassette upon induction that led to cell lysis. However, Applicant only confirmed the overexpression for LysA. The difference of the Shine-Dalgarno (SD) sequence of these three genes in the plasmid pAHB might explain the low expression levels for LysB and Holin. The SD sequence plays a role during a translation initiation as a ribosomal binding site, and a positive correlation between SD sequence and gene expression level has been identified in prokaryotes. The consensus SD sequence (AGGAGG) of E. coli is more effective than the shorter SD sequence, leading to a high level of gene expression. This correlation might be applied to the gene expression characteristics of Rhodococcus. In the plasmid pAHB, the lysA gene has the SD sequence of pTipQC2 (GAAGGAG), which is strong for the gene expression in Rhodococcus, leading to the high expression level of LysA. However, the lysB and Holin genes possess the shorter and weaker SD sequences derived from phage D29: AGGA and GGA, respectively. This difference of the SD sequence might result in overexpression of lysA than the other two lytic genes, resulting in a thicker band of LysA on the SDS-PAGE gel. In any case, despite the low expression of LysB and Holin, PD631pAHB exhibited cell lysis and release of the intracellular components upon induction.

Example 1.11. Characterization of Newly Developed Salt-Tolerant Strains PD631S and PD631pAHB Two salt-tolerant strains PD631S and PD631SpAHB were developed after ten times of successively subculturing PD631 and PD631pAHB on LB agar containing 3% NaCl or 3% NaCl and 35 mg/L CAM, respectively. The growth rates and doubling times of these strains were compared to those of non-salt-tolerant strains PD631 and PD631pAHB. PD631S was able to grow in liquid medium containing 3%

NaCl, with a decreasing doubling time of 5.8 h for the 1st subculture to 3.9 h for the 3rd subculture. When grown without salts, PD631S showed a similar growth rate to that of strain PD631, i.e., a doubling time of 2.1 h for PD631S vs. a doubling time of 2.2 h for strain PD631. This indicated that PD631S can survive under high saline conditions for non-sterile cultivation while producing TAGs. PD631pAHB and PD631SpAHB also grew slower than that of strain PD631, as evident by their doubling times (i.e., 3.2 h for both PD631pAHB and PD631SpAHB and 2.2 h for PD631). To examine the stability of the plasmid pAHB in the newly constructed strain PD631SpAHB, this strain was successively cultured in LB medium without CAM for five generations before checking their ability to grow in LB medium with CAM. The plasmid pAHB was detected in the 5th generation culture, suggesting that pAHB was stable in strain PD631SpAHB in the absence of CAM.

Figure 4A:
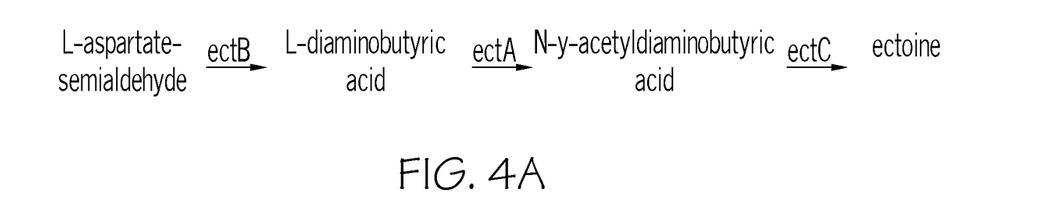
FIG. 4A illustrates that the ectoine synthesis pathway starts from the conversion of L-asparate-semialdehyde to L-diaminobutyric acid, N-gama-acetyldiaminobutyric acid, and then to ectoine. The genes involved in the synthesis steps in this pathway are ectA encoding diaminobutyric acid acetyltransferase, ectB encoding diaminobutyrate-2-oxoglutarate transaminase, and ectC encoding ectoine synthesis.

Example 1.12. Effects of Salts on Non-Sterile Cultivation of Strain PD631S and Its TAG Production Experiments for this Example were conducted to determine the enzymes involved in the synthesis of common osmolytes in strain PD631S under high salt conditions. Among the osmolytes, ectoine is commonly used to provide osmotic balance under extreme conditions. Three genes involved in ecotine synthesis are ectA, ectB, and ectC encoding diaminobutyric acid acetyltransferase, diaminobutyrate-2-oxoglutarate transaminase, and ectoine synthase, respectively (FIG. 4A). Glutamate is another common osmolyte that can be increased as a counter-ion in cells in response to hyperosmotic stress.

Figure 4B:
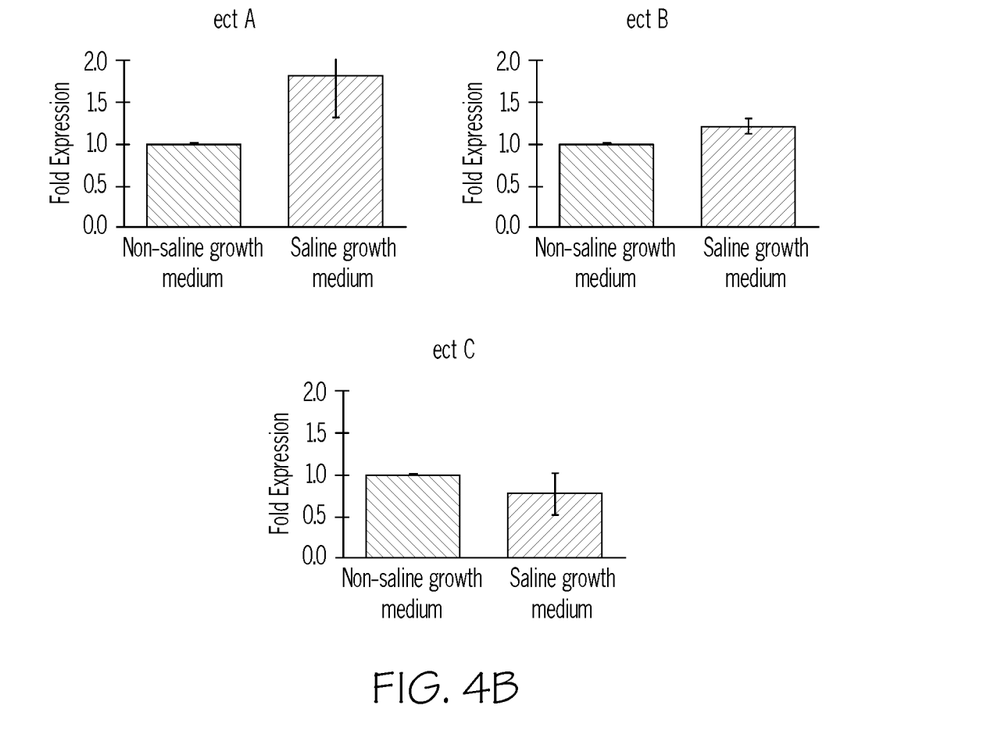
FIG. 4B illustrates salt effects on expression of three ectoine synthesis genes in strain PD631S. Left bars indicate PD631S grown on glucose as a carbon source in non-saline AMS medium. Right bars indicate PD631S grown on glucose as a carbon source in AMS medium with 3% NaCl. All experiments were conducted in duplicate.

Different transcription levels of ectoine synthesis genes in PD631S grown with or without 3% NaCl were observed. Interestingly, as shown in FIG. 4B, the ectA expression level in saline grown PD631S was two-fold higher than that in the non-saline grown PD631S. The mRNA levels encoding ectB was slightly increased while the ectC expression level was slightly decreased in saline grown PD631S. Unlike those observed for ectoine synthesis genes, the expression levels of glutamate synthesis genes (i.e., mRNA levels encoding glutamate synthesis) in saline-grown PD631S were similar to those in non-saline grown PD631S, suggesting that glutamate might not play a key role in PD631S when grown under saline conditions. The gene expression levels for ectoine and glutamate synthesis proteins suggested that ectoine was the key osmolyte produced in PD631S under high salts conditions. Decreased expression levels of ectC was observed.

The effects of two cultivation variables, sterilization of growth medium and presence of 3% NaCl, on the growth of and TAG production by PD631 and PD631S (Table 2) were examined. In sterilized salt-free media, PD631 produced 22.9 mg/L TAG under the conditions of the experiment; the addition of 3% NaCl reduced the production of TAG to 15 mg/L and significantly retarded the growth rate from 0.08 $h^{-1}$ to 0.04 $h^{-1}$. The final optical density of PD631 in salt media was about two times lower than that of PD631 in salt-free media. Also, in the preliminary experiment for this Example, only inoculated PD631 from the saturated culture could grow with 3% NaCl while it could not grow directly from a single colony. In contrast, the amounts of TAG production by PD631S in sterilized salt-free media was slightly less (15.5 mg/L) but maintained its growth rate in the high salts as 0.05 $h^{-1}$ from 0.06 $h^{-1}$.

Table 2, shown below, illustrates TAG production from PD631 or PD631S cultivated with 1% of glucose in AMS medium with or without salts under sterile or non-sterile conditions. All experiments were conducted in duplicate.

TABLE 2

| | Variables | | Growth | | Total TAG |
|---|---|---|---|---|---|
| Experiment | Culture | % NaCl (w/v) | Sterilization | Rate ($h^{-1}$) | TAG (mg/L) | Mass (mg) |
| # a | PD631 | 0 | Yes | 0.08 | 22.9 ± 4.6 | 1.2 ± 0.2 |
| # b | PD631 | 0 | No | 0.08 | 0 | 0 |
| # c | PD631 | 3 | Yes | 0.04 | 15.0 ± 0.4 | 0.8 ± 0.0 |
| # d | PD631 | 3 | No | 0.07 | 4.9 ± 1.6 | 0.2 ± 0.1 |
| # e | PD631S | 0 | Yes | 0.06 | 15.5 ± 0.9 | 0.8 ± 0.0 |
| # f | PD631S | 0 | No | 0.06 | 0 | 0 |
| # g | PD631S | 3 | Yes | 0.05 | 9.8 ± 1.6 | 0.5 ± 0.1 |
| #h | PD631S | 3 | No | 0.05 | 8.0 ± 2.1 | 0.4 ± 0.1 |

The advantage of using PD631S for TAG production is that under non-sterile high salt conditions, which is not necessary to sterilize the growth media to achieve efficient TAG accumulation. PD631S in non-sterilized salt media produced 8.0 mg/L TAGs (52% of that achieved in sterilized salt-free media) while PD631S in non-sterile salt-free media did not produce any TAGs, suggesting that PD631S in non-sterilize salt-free media might be contaminated. The TAGs produced by PD631S in non-sterilized saline growth media were 3 times lower than those produced by PD631 in sterilized no-salt growth media. The differences in the total TAG yields can be explained by the differences in cell densities in both cultures at the time harvested for TAG measurements. The optical density of PD631S in non-sterilized saline growth media (#h) was 3 times lower than that of PD631 in sterilized no-salt growth media (#a). In contrast, PD631 in non-sterile salt media only produced 4.9 mg/L TAGs (22% of that achieved in sterilized salt-free media) while there was no TAGs production from PD631 in non-sterile salt-free media. This indicates that PD631S showed a better ability to survive in non-sterile salt media than PD631 due to adaptive evolution.

Figure 5:
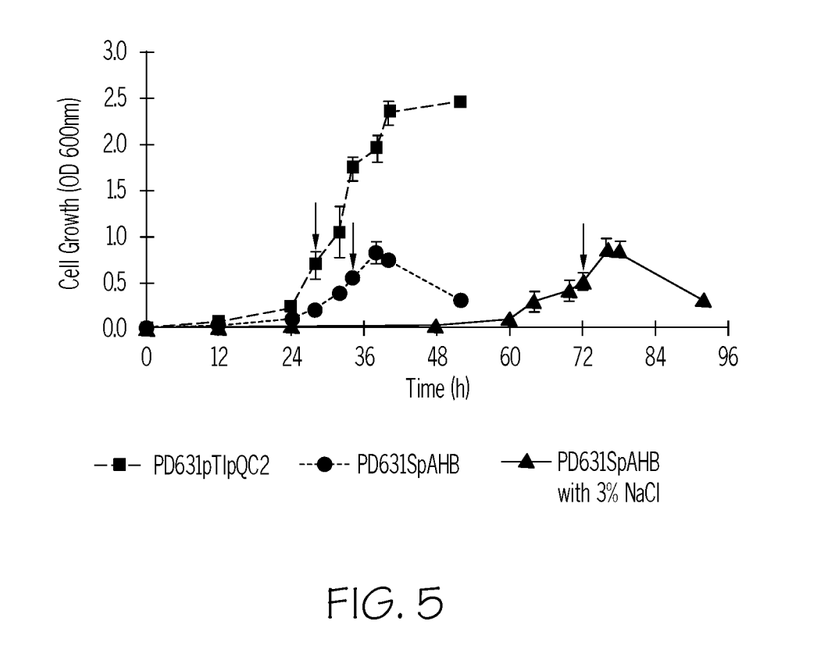
FIG. 5 illustrates that delayed growth of PD631SpAHB in saline growth was observed. Inducible lysis of PD631SpAHB grown in either non-saline or saline medium was observed, based on decrease of optical density 6 h following addition of thiostrepton (an inducer). PD631pTipQC2 was used as a control. Arrows indicate the time point in the OD600=0.5-0.7, growth stage where 1 µg/mL of thiostrepton was added to induce expression of phage lytic genes. All experiments were conducted in duplicate.

Example 1.13. Demonstration of Cell Lysis of PD631SpAHB and TAG Release from PD631pAHB Cell lysis of PD631SpAHB was confirmed based on a decrease of cell density following induction with thiostrepton. As shown in FIG. 5, in the absence of salts, PD631SpAHB grew slower than those of PD631pTipQC2. The strain PD631SpAHB showed a long lag phase of 48 h when grown in saline liquid medium from a colony on LB agar containing 3% NaCl and 35 mg/L CAM. The long lag phase might be due to a hyperosmotic pressure imposed on the strain in saline liquid medium even the strain has already adapted to the saline conditions on agar plates. After adding thiostrepton (1 μg/mL) at 28 h (FIG. 5), PD631pTipQC2 continued to grow up to an optical density of 2.5. However, 6 h after induction with thiostrepton (1 μg/mL), the optical density of PD631SpAHB (regardless of the cultivation conditions) decreased from 0.8 to 0.3. The decrease of optical density after induction was similar to those observed in the induction experiments using PD631pAHB (FIG. 3A). Also, after overnight induction, cell debris of PD631SpAHB was found in the cell culture. Phage lysis proteins in the supernatants of induced PD631SpAHB were also observed on SDS-PAGE gels, providing evidence that phage lysis proteins produced in PD631SpAHB caused cell lysis. Similar to the SDS-PAGE results of induced PD631pAHB, it was shown that the overexpression of LysA and expression of Holin and LysB in induced PD631SpAHB. Overall, the results showed that cell lysis of PD631SpAHB can be effectively controlled by expressing the phage lytic gene cassette at the desired time, preferably after cells have accumulated a high level of TAGs.

The effects of phage lytic gene cassette on cell growth, TAG production, and TAG release of PD631SpAHB were examined and are summarized in Table 3. PD631pTipQC2 in sterilized salt-free media was used as a control. In sterilized media, PD631SpAHB produced similar amounts of total TAG with that from PD631pTipQC2, but slightly decreased the growth rate to 0.15 $h^{-1}$ in salt media and 0.10 $h^{-1}$ in salt-free media. TAG was produced by PD631SpAHB in non-sterilized salt media up to 17.6 mg/L while PD631SpAHB in non-sterilized salt-free media did not produce TAG. After adding additional nitrogen source and inducer, decreased optical densities were observed in the samples with PD631SpAHB decreased but not in the samples with PD631SpAHB grown in non-sterilized salt-free media, suggesting that cell lysis occurred by the expression of phage lytic genes. As the controls, the addition of nitrogen source and inducer did not lyse PD631pTipQC2, instead, the cells grew up to an optical density of 3.5. Also, 21-38% of the total TAGs were released from PD631SpAHB in sterilized media to the supernatant after the induction of phage lysis proteins while only 6% of the total TAGs were released from PD631SpAHB in non-sterilized salt media.

Table 3, shown below, illustrates non-sterile cultivation, TAG production, and TAG release from PD631SpAHB with different growth conditions. All experiments were conducted in AMS medium with 1% of glucose as a carbon source.

sterile medium during the cultivation, leading to reduction of the overall costs and energy inputs for production of bacterial TAGs.

Unlike Gram-negative bacteria that have a thin layer of peptidoglycan (PG) in their cell wall, Gram-positive bacteria are characterized by a thick layer of PG in their cell wall composition. Some Gram-positive bacteria like *Rhodococcus opacus* have a complex cell wall structure containing not only a thick PG layer but also a layer of arabinogalactan, and an outer layer of mycolic acid (MA), making breaking the *Rhodococcus* cells difficult. Accordingly, more phage lysis proteins are needed during infection to open the cell envelope of *Rhodococcus* strain than that for Gram-negative bacteria. Mycobacteriophages are well-studied phages capable of lysing *Mycobacterium* which has a similar cell wall structure of *Rhodococcus*. To lyse the cell wall of *Mycobacterium*, mycobacteriophages use three phage lysis proteins: an endolysin to disrupt PG, a mycolate esterase to digest MA, and a holin to create a hole on the cell membrane to release the endolysin and the mycolate esterase outside of the cell. Accordingly, to lyse *Rhodococcus* cells, three phage lysis proteins are required—endolysin, holin, and mycolate esterase. In this Example, these corresponding phage lytic genes were successfully constructed as an inducible phage lytic gene cassette plasmid (pAHB) and expressed in the TAG-filled PD631SpAHB for TAGs release. This is the first study reporting the successful internal application of phage lysis proteins to lyse *Rhodococcus* for TAGs extraction.

Applicant's results showed that 38% of the total TAGs were released from PD631SpAHB. This TAG release result was similar to the previous finding that about 30% of the total TAGs were released from phage-infected PD631 cells. Different from the bacteriophage infection study, the timing of cell lysis can be controlled and there is no need to prepare an additional phage culture for infection in this Example. However, the TAG release percent observed in this Example

TABLE 3

| | | Variables | | Growth | Total | TAG in | Released |
|---|---|---|---|---|---|---|---|
| Experiment | Culture | % NaCl (w/v) | Sterilization | Rate ($h^{-1}$) | TAG (mg/L) | Pallet (mg/L) | TAG* (mg/L) |
| I | PD631pTipQC2 | 0 | Yes | 0.19 | 24.2 | 24.2 | 0 |
| Ii | PD631SpAHB | 3 | Yes | 0.15 | 24.7 | 19.4 | 5.3 |
| Iii | PD631SpAHB | 0 | Yes | 0.10 | 24.2 | 15.1 | 9.1 |
| Iv | PD631SpAHB | 0 | No | 0.24 | 0 | 0 | 0 |
| V | PD631SpAHB | 3 | No | 0.13 | 17.6 | 16.7 | 0.9 |

*Released TAG were detected in the supernatant of each culture.

Example 1.14. Discussion

Only a few bacterial species are reported as oleaginous strains including Gram-positive species such as *Dietzia, Mycobacterium, Nocardia, Rhodococcus*, and *Streptomyces*. Among oleaginous bacteria, *Rhodococcus opacus* PD630 is recognized as a model TAG-accumulating strain due to its ability to produce up to 76% of its cell dry weight. Applicant's results indicate that the newly constructed *Rhodococcus* strain PD631SpAHB is a promising candidate to address the two major challenges of current biolipid-based biofuel production—high costs associated with sterilization cultivation and TAGs extraction. As many microorganisms, except halophilic bacteria, are unable to survive under 3% NaCl conditions, the salt-tolerant characteristics of PD631SpAHB is advantageous because it removes the need of the use of was lower than those using solvent-based TAGs extraction process from *Rhodococcus* strain (i.e., over 55% of TAG extraction efficiency). In a previous study, TLC analysis revealed that most TAGs were still not released into the supernatant but associated with pellets of cell debris, suggesting that TAG granules are trapped with the cell debris or TAGs are attached to the cell membranes. This phenomenon was also observed in Applicant's Example. Accordingly, further improvements are readily envisioned to increase TAGs yields and/or recover attached TAGs on the cell debris or the cell membranes.

The levels of TAG accumulation in oleaginous bacterium like *R. opacus* PD630 are known to be affected by several factors such as carbon/nitrogen (C/N) ratios, types of carbon and/or nitrogen sources, and different cultivation methods (single-stage or two-stage). Accordingly, higher levels of TAG accumulation in PD631SpAHB can be achieved by modifying C/N ratios, carbon, and nitrogen sources in the growth medium. In this Example, the newly constructed PD631SpAHB was grown on glucose at a much lower C/N ratio of 28 using two-stage cultivation strategies (i.e., growing up to the stationary phase, followed by TAG accumulation under nitrogen-free conditions). By using gluconate as a carbon source and ammonium chloride as a nitrogen source in the sterile saline medium with a higher C/N ratio of 147, enhanced TAG production by PD631SpAHB up to 4-fold higher than of the strain grown on glucose and a low C/N ratio of 28.

Different time to lyse the cells is likely to result in different levels of TAG release, as cell lysis timing by phage is tightly regulated inside cells and actively growing host cells might be needed to produce phage lytic proteins for effective cell lysis. Thus, to check the cell lysis timing, Applicant first monitored the cell lysis based on the decrease of optical density after the addition of inducer, thiostrepton and nitrogen source. The addition of nitrogen was to bring stationary stage cells into actively growing cells. As shown in FIG. 3A, it was confirmed that overnight induction would bring the maximum cell lysis. Thus, the other cell lysis experiments in this Example were conducted overnight. To examine if phage lytic proteins can be effectively produced by non-growing PD631SpAHB, Applicant used thiostrepton as an inducer without an additional nitrogen source and observed an increase of TAG release (from 38% up to 51% of the total TAGs) from the strain PD631SpAHB. This increased TAGs release percent is comparable to the amounts of TAGs extracted from *Rhodococcus* strain via solvent-based extraction process (i.e., ~55%). Applicant's results suggested that minimization of TAG utilization in cells before cell lysis is a factor in obtaining high TAG yields. Conditions for optimal cell lysis is further envisioned.

After cells were lysed by phage lytic proteins, the TAGs of the newly developed strain (PD631SpAHB) were either released into the supernatant or attached to the cell debris. The TAGs in the supernatant can be theoretically separated from water easily because TAGs are immiscible and have a lighter density than water. The lighter density of TAGs will allow TAGs to float on the surface of water, and this effect is expected to be more pounced in high saline solution. In fact, floating lipid droplets on the surface of the supernatant of lysed cells after centrifugation have been observed in Applicant's cell lyse experiments.

As a substantial amount of the TAGs was attached to cell debris after cell lysed, the TAGs from the cell debris should be recovered. Previous studies have shown that extraction time and/or the amounts of solvents required for TAGs extraction can be reduced if cell disruption is in advance. Also, a recent study showed that lipids from *Nannochloropsis* sp. were recovered by only adding non-polar solvent hexane (which is less toxic than chloroform that is commonly used in TAG extraction), due to the ultrasonication treatment for cell disruption. Another possible method to recover the TAGs from the lysed cells is through direct transesterification to convert TAGs into biodiesel (i.e., fatty acid methyl esters). Additionally, a recent study demonstrated increases in biolipid release percent (up to 73%) from microalgae by using a combination of autolysin and trypsin to cleave chloroplasts and lipid bodies inside the cells, and recovery of the released lipids via centrifugation from the medium without using a solvent. All these approaches can potentially be applied to recover the TAGs attached on phage-protein-lysed cell debris to increase TAGs yield, leading another path to reduce lipid-based biofuel production costs. As such, methods to recover the TAGs from the cell debris are readily envisioned.

This Example focuses on the non-sterilize cultivation of engineered oleaginous strain for TAGs production and extraction, addressing important challenges to be overcome in order to reduce the overall biolipid-based biofuel production cost. Firstly, cost reduction in cultivation of oleaginous strain can be realized by using Applicant's novel non-sterile cultivation in high salt solution. Additionally, as TAGs density is lower than water, once TAGs are released from cells into liquid medium, TAGs are expected to float to water surface for easy recovery. This phenomenon is expected to occur when Applicant's phage-lytic-protein-based approach is applied—i.e., PD631SpAHB lysed and TAGs are released from PD631SpAHB into the supernatant spontaneously, resulting in the reduction of lipid-based biofuel production costs due to a less solvent usage, wet biomass extraction, and/or no additional cell disruption step.

The energy operation cost per liter of biodiesel produced from microbial oil was estimated to be 16.4% for sterilization, 20.6% for harvesting/cell disruption (i.e., decantation and cell disruption), and 6.7% for solvent-based TAGs extraction. By using Applicant's newly developed PD631SpAHB for TAGs production and release, although centrifugation is still needed for separating cell debris from the supernatant, this process is expected to save at least 37% of total energy costs from sterilization and harvesting/cell disruption and reduced the amounts of solvent. This simple analysis suggests that PD631SpAHB is a promising candidate for the non-sterile cultivation for TAG production and extraction, leading to a reduction of the production costs of biolipid-based biofuel.

Overall, Applicant's novel approach using phage lysis enzymes combined with non-sterile cultivation has a significant impact on biofuel production costs and environmental issues, comparing to the traditional cultivation and solvent extraction processes. Nevertheless, the cultivation condition for maximizing TAG production and other induction strategy to minimize TAG utilization by the TAG-filled PD631SpAHB during the induction of cell lysis are readily envisioned. This is the first report of the non-sterile cultivation of *Rhodococcus opacus* for biolipids production and application of phage lytic proteins to lyse cells for biolipid extraction. The findings demonstrated in this Example provide the groundwork for an efficient biolipid production and extraction from *Rhodococcus* strain.

Example 1.15. Conclusions

This Example has successfully demonstrated non-sterile TAGs production and release using a newly developed salt-tolerant PD631SpAHB. The inducible plasmid carrying a phage lytic gene cassette (pAHB) enabled lysis of TAG-filled PD631SpAHB to release TAGs into liquid medium. This technique offers a new method for biolipid extraction, leading to a reduction of overall extraction costs of biolipid for biofuel production. The high salt-tolerant characteristics of PD631SpAHB remove the need of using sterile medium for TAG cultivation. Overall, these results indicate that this new strain, PD631SpAHB, is a promising candidate to address the two major challenges of current biolipid-based biofuel production—high costs associated with sterilization cultivation and TAGs extraction.

Without further elaboration, it is believed that one skilled in the art can, using the description herein, utilize the present disclosure to its fullest extent. The embodiments described herein are to be construed as illustrative and not as constraining the remainder of the disclosure in any way whatsoever. While the embodiments have been shown and described, many variations and modifications thereof can be made by one skilled in the art without departing from the spirit and teachings of the invention. Accordingly, the scope of protection is not limited by the description set out above, but is only limited by the claims, including all equivalents of the subject matter of the claims. The disclosures of all patents, patent applications and publications cited herein are hereby incorporated herein by reference, to the extent that they provide procedural or other details consistent with and supplementary to those set forth herein.

What is claimed is:

1. An oleaginous bacterium comprising:
   lipids; and
   at least one exogenous and inducible gene,
      wherein the exogenous and inducible gene encodes at least one protein that induces lysis in the oleaginous bacterium to release the lipids, and
      wherein the oleaginous bacterium exhibits tolerance to growth at salt concentrations of at least 3% (w/v) when cultured in non-sterile conditions, and wherein the oleaginous bacterium is selected from the group consisting of R. opacus strain PD631SpAHB, R. opacus strain PD631S, and combinations thereof.

2. The oleaginous bacterium of claim 1, wherein the lipids are selected from the group consisting of triacylglycerols, biolipids, polyhydroxyburyrate, and combinations thereof.

3. The oleaginous bacterium of claim 1, wherein the lipids are released from the oleaginous bacterium into an environment upon expression of the protein by the exogenous and inducible gene.

4. The oleaginous bacterium of claim 1, wherein the exogenous and inducible gene encodes a protein selected from the group consisting of endolysin, holin, mycoesterase, lytic proteins, and combinations thereof.

5. The oleaginous bacterium of claim 1, wherein the exogenous and inducible gene encodes a lytic protein, wherein the lytic protein degrades a cell envelope of the oleaginous bacterium.

6. The oleaginous bacterium of claim 1, wherein the exogenous and inducible gene comprises at least one phage gene.

7. The oleaginous bacterium of claim 1, wherein the exogenous and inducible gene is on a plasmid.

8. The oleaginous bacterium of claim 1, wherein the exogenous and inducible gene is integrated into a chromosome of the oleaginous bacterium.

9. A method of releasing lipids into an environment, the method comprising: introducing at least one oleaginous bacterium of claim 1 to the environment, and inducing expression of the at least one gene to thereby express the at least one protein, wherein the at least one protein facilitates the lysis of the oleaginous bacterium and release of the lipids into the environment.

10. The method of claim 9, wherein the introducing comprises inoculating the environment with the oleaginous bacterium.

11. The method of claim 10, wherein the environment is a non-sterile environment.

12. The method of claim 11, wherein the non-sterile environment comprises a salt concentration of at least 3% (w/v).

13. The method of claim 10, wherein the non-sterile environment lacks antibiotics.

14. The method of claim 9, wherein the lipids are selected from the group consisting of triacylglycerols, biolipids, polyhydroxyburyrate, and combinations thereof.

15. The method of claim 9, wherein the gene encodes a protein selected from the group consisting of endolysin, holin, mycoesterase, lytic proteins, and combinations thereof.

16. The method of claim 9, wherein the gene comprises at least one phage gene.

17. The method of claim 9, wherein the gene is on a plasmid.

18. The method of claim 9, wherein the gene is integrated into a chromosome of the oleaginous bacterium.

19. The method of claim 9, wherein the inducing occurs by introducing an inducing agent or condition into an environment.

20. The method of claim 9, wherein the protein promotes a lytic cycle to thereby degrade a cell envelope of the oleaginous bacterium and lyse the cells.

21. The method of claim 9, wherein the release of the lipids into the environment occurs without use of a solvent.

22. The method of claim 9, wherein the tolerance to salt is represented by a growth rate that is at least 10% similar when the oleaginous bacterium is grown at 30° C. in the presence or absence of at least 3% (w/v) salt.

* * * * *